United States Patent [19]

Anderson

[11] 4,249,897
[45] Feb. 10, 1981

[54] MODULAR CUSHIONING ORTHODONTIC BRACKET STRUCTURE

[76] Inventor: Roland M. Anderson, 1616 SW. Sunset Blvd., Portland, Oreg. 97201

[21] Appl. No.: 870,204

[22] Filed: Jan. 17, 1978

[51] Int. Cl.³ .............................................. A61C 3/00
[52] U.S. Cl. .......................................... 433/8; 433/16
[58] Field of Search ................. 32/14 A; 433/8, 9, 10, 433/11, 12, 13, 14, 15, 16, 17

[56] References Cited

U.S. PATENT DOCUMENTS

| | | | |
|---|---|---|---|
| 2,908,974 | 10/1959 | Stifter | 32/14 A |
| 3,052,027 | 9/1962 | Wallshein | 32/14 A |
| 3,464,113 | 9/1969 | Silverman et al. | 32/14 A |
| 3,964,165 | 6/1976 | Stahl | 32/14 A |
| 4,107,844 | 8/1978 | Kurz | 32/14 A |
| 4,186,488 | 2/1980 | Wallshein | 433/8 |

Primary Examiner—Gene Mancene
Assistant Examiner—John J. Wilson
Attorney, Agent, or Firm—Kolisch, Hartwell & Dickinson

[57] ABSTRACT

Modular orthodontic bracket structure including a pair of releasably interengageable bracket members. One of these members, which forms an outer member, has a relatively high degree of elastic stiffness. This outer member includes ligating posts which define a socket for snap-receiving the other, or inner, member. The inner member has a lower degree of elastic stiffness, and includes a slot for receiving an arch wire. The slot is shaped to define the particular positional orientation of an arch wire received therein so as to effect the transmission of a prescribed force from the wire to the outer bracket member, and then to a tooth.

4 Claims, 18 Drawing Figures

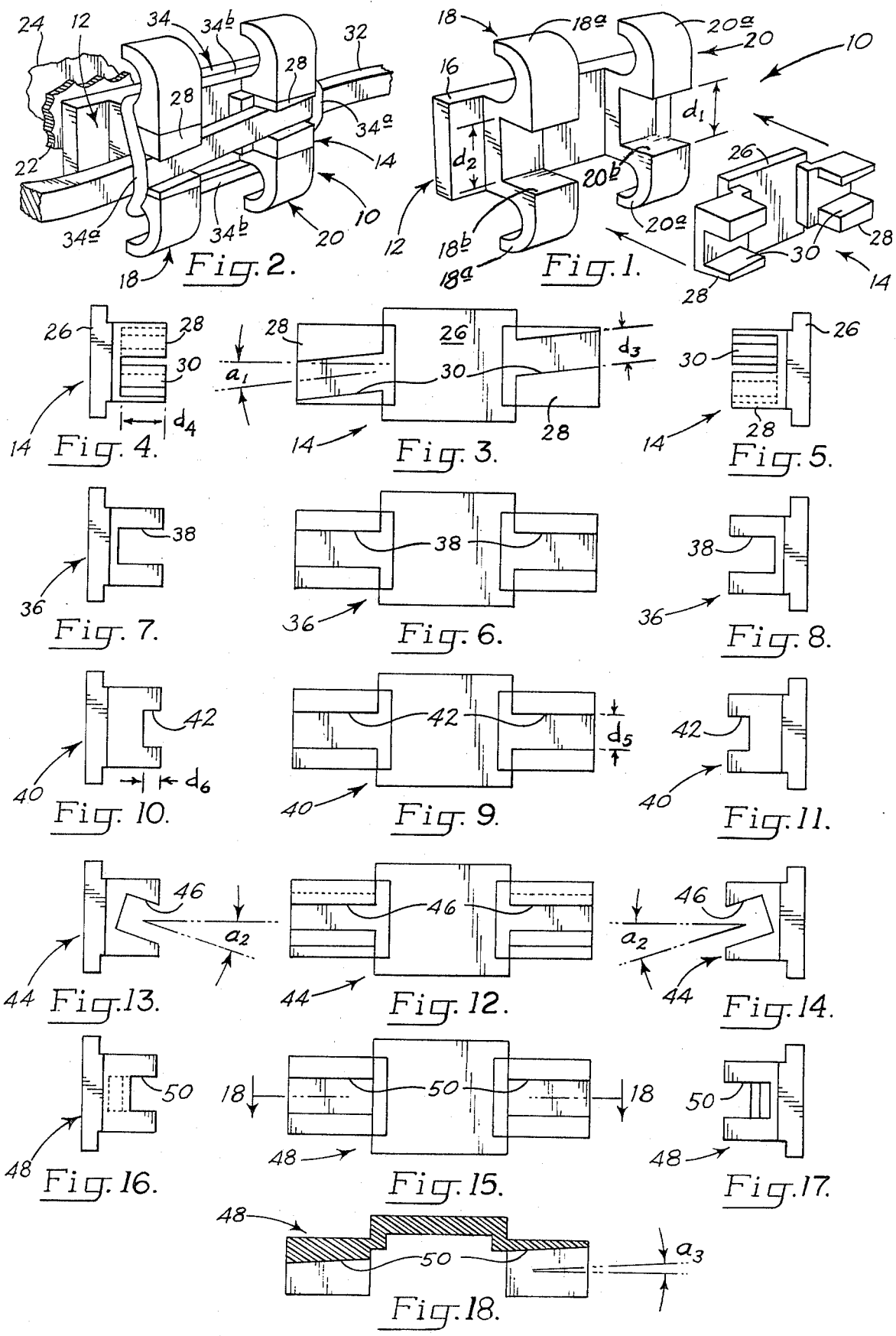

MODULAR CUSHIONING ORTHODONTIC BRACKET STRUCTURE

BACKGROUND AND SUMMARY OF THE INVENTION

This invention pertains to a modular, cushioning orthodontic bracket structure mountable on a conventional orthodontic tooth band. More particularly, it concerns such a structure which includes outer and inner releasably interengageable bracket members that are formed of materials having different degrees of elastic stiffness.

As is well understood, orthodontics involves the application of forces to teeth to change their positions and/or orientations in the mouth. Typically, a bracket is fastened to a tooth, with a band or by direct bonding to the enamel of the tooth. The bracket is for the purpose of receiving a force-inducing arch wire. A widely used orthodontic technique, in the setting of such apparatus, involves the preshaping or bending of an arch wire at the location of selected tooth brackets so that appropriate forces are applied to the associated teeth when the wire is tied, or ligated, to the particular brackets. Another technique which has been proposed involves the use of an insert in a tooth bracket, which insert is formed with an angled or rotated slot that receives an arch wire. In this kind of a setting, pre-bending of an arch wire at the location of such an insert is not necessary. Rather, insertion of the arch wire in such a slot deforms the arch wire which, as it tries to restore its position, applies a tooth-positioning force.

These prior techniques, however, do not adequately deal with the problem of shock that occurs to teeth newly exposed to a tooth-positioning force. More specifically, these prior art techniques involve extremely rigid structures which can, and most often do, result in a significant amount of discomfort shortly after the affixing of an arch wire. Further, the rigid and tight connections which have existed heretofore between conventional arch wires and bracket structures usually produce a relatively high-friction condition which tends to impede, in some instances, movement of a tooth. This results from binding between an arch wire and bracket.

A general object of the present invention is to provide a novel modular, cushioning orthodontic bracket structure which offers all of the advantages of the above-discussed prior art techniques, while significantly minimizing the disadvantages.

More specifically, an object of the invention is to provide such a bracket structure which minimizes tooth shock and discomfort, and which maximizes low-friction movability of a tooth along an arch wire.

According to a preferred embodiment of the invention the proposed bracket structure includes outer and inner releasably interengageable bracket members. The outer bracket member has the form, generally, of a conventional so-called standard-twin edgewise bracket of the type first discussed above, with this member being formed from a material having a relatively high degree of elastic stiffness. This outer member, when used, is secured as by welding to a conventional tooth band, or to a direct bonding pad and includes a special socket for snap-receiving the inner member in the structure. In particular, this socket is intended to capture a received inner member in what is referred to herein as an omnidirectionally fixed-captured manner. In other words, while removal of a received inner member is possible, when the member is in place it is substantially firmly held against any significant movement in any direction relative to the outer member.

The inner member, conversely, is formed of a material having an appreciably lower degree of elastic stiffness. This member includes a slot for receiving a conventional arch wire. The slots, in certain particular inner members, are shaped to define the specific positional orientation of an arch wire received therein, so as to effect, through deforming the arch wire, the transmission of predetermined forces from the wire to an outer bracket member, and thence to an associated tooth.

With such a construction, pre-bending of an arch wire, according to the prior-art technique first-described above, is not necessary. Further, a tooth-positioning force is transmitted in such a manner as to minimize shock. For example, with initial installation of an arch wire, resiliency in the lower-stiffness inner member deforms to store a significant amount of potential energy due to the force exerted by the arch wire as it tends to restore its undeformed condition. This action greatly reduces the discomfort-producing effects of arch wire installation. This more pliant inner member, through such energy storage, promotes the continual and gradual application of a corrective force.

Also, materials which have been found to function well for forming the inner member in the proposed structure have also been found to offer relatively low-friction contact with an arch wire. This, of course, minimizes the binding problem mentioned above, and facilitates tooth movement along an arch wire.

These and other objects and advantages which are obtained by the invention will become more fully apparent as the description which now follows is read in conjunction with the accompanying drawings.

DESCRIPTION OF THE DRAWINGS

FIG. 1 is a front perspective view illustrating one modification of outer and inner bracket members which form part of the present invention—these members being shown in exploded or disassembled form.

FIG. 2 is a front perspective view, on about the same scale as FIG. 1, showing the bracket members of FIG. 1 in assembled form, mounted on a tooth band, and ligated to a run of an orthodontic arch wire.

FIG. 3 is an enlarged front elevation showing details of construction of the inner bracket member of FIGS. 1 and 2.

FIGS. 4 and 5 are left and right end elevations, respectively, of the bracket member shown in FIG. 3.

FIG. 6 is a front elevation of a second modification of an inner bracket member constructed according to the invention; and FIGS. 7 and 8 are end elevations like FIGS. 4 and 5.

FIG. 9 is a front elevation of a third modification of an inner bracket member constructed in accordance with the invention; and FIGS. 10 and 11 are end elevations like FIGS. 4 and 5.

FIG. 12 is a front elevation of another modification of an inner bracket member constructed in accordance with the invention; and FIGS. 13 and 14 are end elevations like FIGS. 4 and 5.

FIG. 15 is a front elevation of still another modification of an inner bracket member in accordance with the invention; and FIGS. 16 and 17 are end elevations like FIGS. 4 and 5.

FIG. 18 is a cross-sectional view taken generally along the line 18—18 in FIG. 15.

DETAILED DESCRIPTION OF THE INVENTION

Turning now to the drawings, and referring first to FIGS. 1 and 2, indicated generally at 10 is an orthodontic bracket structure, including outer and inner bracket elements, or members, 12, 14, respectively, constructed in accordance with the present invention. Bracket member 12 is also referred to herein as a first bracket member, and also as a second force-transmitting element. Bracket member 14 constitutes a second bracket member, and also a first force-transmitting element.

Considering first the construction of outer bracket member 12, it includes an elongated generally flat base 16 from the front side of which protrude two laterally spaced post structures 18, 20. Element 12 preferably is formed in any suitable manner as a unitary member of a relatively stiff, rigid, low-elasticity material such as stainless steel. This material has the relatively large elastic stiffness. Post structure 18 includes a pair of vertically spaced, rearwardly curving posts 18a located on opposite sides of a slot 18b. Similarly, post structure 20 includes a pair of vertically spaced, rearwardly curving posts 20a disposed on opposite sides of a slot 20b.

Although different specific dimensions may be used in the construction of an outer bracket member 12, certain specific dimensions, mentioned hereinbelow, have been found to be extremely satisfactory in many instances. More particularly, the distance between the near face of post structure 18 (in FIG. 1) and the far (hidden) face of post structure 20, which faces are disposed in parallel planar relationship, is about 0.135-inches. The distance between the confronting faces of the two post structures, which faces are disposed in parallel planar relation with the other two faces just mentioned, is about 0.055-inches.

Slots 18b, 20b are aligned along an axis which substantially parallels the longitudinal axis of base 16. Each of these slots has the same dimensions. More particularly, the front-to-rear depth of each slot is about 0.040-inches, the height of each slot at the front thereof, shown at $d_1$, is about 0.050-inches, and the height of each slot at the back thereof, shown at $d_2$, is about 0.051-inches.

The length of base 16 is about 0.155-inches, its height about 0.100-inches and its thickness or depth about 0.010-inches. Finally, the distance between the front face of base 16 and the base of slots 18b, 20b is about 0.015-inches.

Slots 18b, 20b, and the space between the confronting faces of post structures 18, 20, are collectively referred to herein as a socket in member 12. Posts 18a, 20a are referred to as ligation accommodating or anchoring means.

In its general configuration, bracket member 12 is similar to conventional so-called standard-twin orthodontic brackets which are adapted for securing, as by welding, to an orthodontic tooth band or to a direct bonding tooth pad. Referring for a moment specifically to FIG. 2, here, bracket member 12 is shown so mounted on a tooth band (shown fragmentarily) which band is conventionally mounted, as by cementing, on a tooth shown fragmentarily at 24.

As will become more fully apparent from the ensuing discussion, bracket member 14 is one of what might be thought of as a family of modular bracket members which are intended for inserting in the socket mentioned above provided in a bracket member like outer bracket member 12. The basic configurations of all members, like member 14, within this "family", with respect to outside dimensions thereof, are alike. As will become apparent, what differs from one modification of member 14 to another is the orientation, configuration and size of a void space or slot provided therein for receiving a portion or run of an arch wire.

Considering now specifically the construction of inner bracket member 14, the same is a unitary member formed of a quite elastic resilient material, such as nylon or urethane. Such material has a relatively low elastic stiffness—one which is significantly lower than that for stainless steel. One of the important considerations of the present invention is that the resilience, or elasticity, of the material forming an inner member 14 be appreciably less than that of the material forming an outer bracket member 12. Putting this another way, it is desirable that the elastic stiffness of the material making up an inner bracket member be less than that of the material forming an outer bracket member. The reason for the importance of this factor will be explained in detail later.

Bracket member 14 includes an elongated central base 26 from the front face of opposite ends of which project laterally and forwardly a pair of generally block-like extensions, or ears, 28. The overall configuration of this member is believed to be clearly evident from a study of FIGS. 1-5, inclusive.

Member 14 is constructed for what might be thought of as snap-fitment within the "socket" described above which is formed in outer bracket member 12. FIG. 2 in the drawings shows the condition of member 14 being so fitted with member 12. Thus, base 26 has a width which is just slightly less than the spacing between the confronting faces of post structures 18, 20, and a height which is substantially the same as the height of base 16 in member 12. The depth or thickness of base 26 is slightly less than the distance between the front face of base 16 and the forwardly facing portions of slots 18b, 20b. Ears 28, as is most evident in FIG. 2, include portions shaped to fit snugly within slots 18b, 20b, with the outer faces of these portions substantially flush with outer face portions of the posts in member 12. In particular, ears 28 are shaped to complement the slight rear-to-front taper (described above) in slots 18b, 20b. It is this provision which accommodates snap-fitment between members 12, 14.

With member 14 fitted as shown with member 12, the former is releasably locked in what is referred to herein as an omnidirectionally fixed-captured condition. In other words, except for forced removal of the inner member, the same is essentially locked against movement relative to the outer member. Lateral fitment of base 26 between the confronting faces of posts 18a, 20a prevents lateral slippage of member 14 out of place. The slightly underbeveled opposing surfaces of slots 18b, 20b, similarly, prevent fore-and-aft slipping of member 14 out of place.

Further describing inner bracket member 14, this member, and more particularly extensions 28 therein, contain an angled slot 30 (formed by two aligned channels) which is intended to receive a run of a conventional arch wire. As can be seen clearly in FIGS. 1-3, inclusive, slot 30 slopes upwardly and to the right in these figures. While different specific cross-sectional dimensions may be used for slot 30, the same herein has a height, shown at $d_3$ (FIG. 3), of about 0.022-inches, and a depth, shown at $d_4$ (FIG. 4), of about 0.028-inches. These dimensions have been chosen to accommodate a particular size range of conventional orthodontic arch wire materials. It will be evident to those skilled in the art that other specific slot dimensions may be used if desired. In member 14, the longitudinal axis of slot 30, as viewed along a line normal to the front of the member, is disposed at an angle of about 7° relative to the longitudinal axis of the member per se. This angle is indicated at $a_1$ in FIG. 3.

Referring for a moment now particularly to FIG. 2, wherein bracket members 12, 14 are shown in assembled and operative condition, extending through slot 30 is a run 32 of a conventional rectangular-cross-section arch wire having cross-sectional dimensions of about 0.021-inches by about 0.025-inches. Wire run 32 is ligated to bracket structure 10 through the use of elastomeric loop, or band, 34 of the type described in U.S. Pat. No. 3,530,583 and illustrated in FIGS. 1–4, inclusive, therein. In particular, band portions 34a extend over the front side of the arch wire, pulling it into slot 30, with portions 34b in the band caught on the back curved sides of posts 18a, 20a.

Prior to its insertion in slot 30, run 32 of the arch wire is in what might be thought of as an undeformed state. As distinguished from a common prior art technique of placing a permanent deformation in the arch wire at the location of a bracket structure, run 32, in its undeformed pre-insertion condition, is simply inserted in slot 30, with such slot then effecting a deformation in the run. In other words, arch wire run 32 has a natural tendency to extend past structure 10 along a path substantially paralleling what might be thought of as the longitudinal axis of this structure. Thus, because of the slight angular deformation created in the arch wire run after insertion in slot 30, the arch wire has a tendency to restore itself to an undeformed state. As a consequence of this action, a lateral rotational force is introduced into the bracket structure through contact between the arch wire run and inner bracket member 14. This force, in turn, is transmitted through bracket structure 10 and tooth band 22 to tooth 24, tending to rotate the tooth in a clockwise direction as viewed from the front side of the tooth.

Because of the differences mentioned earlier in the elasticities and of the materials making up bracket members 12, 14, some important and unique force-transmitting effects take place. The greater elasticity of the material making up inner member 14 causes this material to "cushion" the transmission of force directly from the arch wire to the tooth. More particularly, the tendency of the arch wire run to restore itself to an undeformed state produces a significantly greater initial deformation in bracket member 14 than in bracket member 12. Put another way, the force exerted on bracket structure 10 by the deformed arch wire run causes potential energy to be stored in the bracket structure for deliverance to the tooth, with a significantly greater portion of this potential energy being stored in the more elastic member 14 in the bracket structure, which member is in direct contact with the arch wire run.

A significant consequence of this situation is that the tooth is subjected to a more gradual and continual angulation action, and hence is subjected to considerably less discomfort than occurs where force is directly transmitted through extremely rigid members. Member 14 acts as a low-elasticity storage unit for potential energy, which energy is delivered at a relatively uniform time-extended rate to change the angular disposition of the tooth. In otherwords, there is a more even and less uncomfortable force application to tooth 24 using bracket structure 10 than is characteristic of prior art techniques.

The greater rigidity of member 12 within structure 10, which member is directly anchored to tooth band 22, affords a firm and rigid ligating "footing", so-to-speak for ligating band 34. Also, it affords a good rigid connection with tooth band 22. Further, it provides a sure force-transmitting back-up support for an inner member like member 14.

Because of the way in which member 14 is omnidirectionally captured within member 12, the relative positions of members 12, 14 remain unchanged throughout force application to a tooth. This feature, also, is important in contributing toward uniform controlled force-application to a tooth.

As was mentioned earlier, the present invention contemplates that a number of different styles, so-to-speak, of inner bracket members may be used with an outer bracket member 12. An inner member like member 14 is one which is designed to produce lateral rotation or angulation of a tooth. More specifically, member 14 is intended to produce generally clockwise rotation of a tooth as the same is viewed from its front side. It will be obvious to those skilled in the art that the axis angle for slot 30 in member 14 may have different specific values to provide for a range of angulation members like member 14. Also, it will be obvious that the angular dispositions of the slot axis and of the member axis may be reversed so that use of an angulation member produces counterclockwise rotation of a tooth as viewed from its front side.

The remaining drawing figures illustrate four other types of inner bracket members which form part of the invention, and which have been found to have particular utility. More specifically, FIGS. 6–8, inclusive, show an inner bracket member 36 which includes a slot 38 that has the same cross-sectional dimensions as previously described slot 30, and whose longitudinal axis parallels the longitudinal axis of member 36 per se. This kind of inner member might be referred to as a "regular" member.

With the exception of the orientation of slot 38 in member 36, the other dimensions and configurational features of the member are substantially identical to those of member 14.

FIGS. 9–11, inclusive show an inner bracket member 40 which is referred to herein as a "lateral inset" member. Formed in member 40 is a slot 42 which is oriented in the member in the same manner as previously mentioned slot 38, but whose cross-sectional shape is quite different. More particularly, the height of slot 42 shown at $d_5$ (FIG. 9) is about 0.022-inches, and the depth of the slot, shown at $d_6$ (FIG. 10) is about 0.015-inches. It is thus apparent that slot 42 is considerably shallower than slots 30, 38.

Insertion of an arch wire run in slot 42 produces a slight forward deformation of the run in the slot, causing the wire to press inwardly against the base of the slot in an attempt to restore itself to an undeformed state. Thus, use of an inner member like member 40 tends to cause inward shifting of a tooth. The force transmitted to the tooth from the arch wire causes deformation of member 42, and hence storage of potential energy in the member. In this respect, member 40 in an outer bracket member like member 12 functions to minimize discomfort, and to promote controlled force application in an even-handed manner, in the same way that was described earlier for inner member 14. It will be obvious that while a particular slot depth has been described for·slot 42, different depths may be used to effect different degrees of lateral inset corrective forces.

FIGS. 12–14, inclusive, show yet another inner bracket member 44 having a slot 46. As is the case with the other inner bracket members so far described, the main dimensions and configuration of member 44 are the same as those described for member 14. The longitudinal axis of slot 46 substantially parallels the longitudinal axis of member 44 per se, but, as can be seen in FIGS. 13 and 14, the slot slopes upwardly progressing rearwardly in member 44. The angle of this slope is shown at $a_2$ in FIGS. 13 and 14, and in the case illustrated is about 18°. The spacing (measured along a "normal" line) between the upper and lower surfaces of slot 46 is about 0.022-inches.

Insertion of a suitable rectangular-cross-section arch wire run in slot 46, with the same installed in an outer bracket member, produces a deforming twist along the axis of the wire run which results in the transmission of what might be thought of as a anterior-posterior torque on a tooth. For example, were member 44 installed in an outer bracket member with the vertical orientation shown for it in FIGS. 12–14, the torque applied to a tooth would be counterclockwise, as viewed from the position of FIG. 13, or clockwise as viewed from the position of FIG. 14. The material making up member 44 performs, in respect to the transmission of a torque force, in the same energy-storing discomfort-reducing manner described earlier for the performance of inner members 14, 40. Obviously, the angle of inclination of slot 46 may have different specific values depending upon the degree of torque force desired. Also, the direction of torque application to a tooth can be in the reverse direction simply by inverting the position of member 44 in an outer bracket member.

FIGS. 15–18 disclose still a further embodiment of an inner bracket member, such being shown at 48, with this member including a slot 50. Inner member 48 is referred to herein as a "rotational" member, and is intended to be used to produce rotation of a tooth about its own longitudinal axis. Thus, slot 50, as viewed from the front of the member (see FIG. 15), lies in the same horizontal plane as the longitudinal axis of the member per se, but, as viewed in FIG. 18, is slightly angled with respect to the member's axis, such angle being depicted as $a_3$. The particular slot 50 which is shown herein has a depth, at the left side of member 48 in FIGS. 15 and 18, of about 0.015-inches, and a depth, at the right side of the member in these figures, of about 0.038-inches. Insertion and ligating of an arch wire run in slot 50 produces a horizontal-plane deformation in the run which, in trying to restore itself, transmits a rotational force to a tooth causing to turn it about its own longitudinal axis. With member 48 positioned as shown in the figures, the direction of such rotation is clockwise as viewed in FIG. 18. It will be obvious that angle $a_3$ may have different specific values. Further, to cause tooth rotation in the reverse direction simply entails reorienting the position of member 48 end-for-end. Again, inner member 48 functions, from the standpoint of energy storage and discomfort reduction, in exactly the same manner described for the other inner members.

It will thus be apparent that a number of significant advantages are obtained through use of the bracket structure described herein. With the materials making up the outer and inner bracket members in the structure having the different elasticities described earlier, cushioning action takes place which minimizes tooth discomfort. Further, important potential energy storage takes place in the more elastic inner bracket member, which storage results in the time-extended, even delivery of tooth-positioning forces. Greater rigidity in the outer bracket member affords a firm ligating footing for "tying in" an arch wire, and for backing up an inserted inner member. Still another important feature is that the material used in the inner bracket member is a low-frictioning material which minimizes the undesirable tendencies, experienced in the past, of an arch wire to bind in a bracket structure. Such binding often has occurred where there is both a sideways pull on a tooth, and a force, or tendency, causing this tooth to angulate or rotate in some direction. Because of the fact that assembly of an inner and outer bracket member results in the former becoming omnidirectionally captured in the latter, the relative positions of these members remains unchanged during force application—a feature which further enhances the evenness of force application to a tooth.

It will also be evident that the bracket structure disclosed herein is of a modular type, wherein a plurality of different specific types of inner bracket members may be inserted in a standardized outer bracket member. Thus, different inner bracket member can, over time, be easily exchanged and inserted in an outer bracket member (which is fastened to the tooth with a fixed relative orientation throughout treatment) so that different kinds of corrective forces can be applied to a particular tooth.

While a preferred embodiment of the invention, with several modifications, has been described herein, it is appreciated that other changes and variations may be made without departing from the spirit of the invention.

It is claimed and desired to secure by Letters Patent:

1. Orthodontic bracket structure for use with an orthodontic arch wire and the like comprising
   a first bracket member of the twin edgewise type formed of a material having one preselected degree of elastic stiffness, and including ligation-anchoring means including a pair of laterally spaced post structures having a pair of confronting, generally upright faces which at least partially define a socket located adjacent said means, and
   a second bracket member removably seatable in an omnidirectional fixed-captured manner within said socket and laterally against said faces, and formed of a material having another preselected degree of elastic stiffness which is less than said one preselected degree, said second member including means defining a void space adapted to receive a run of such an arch wire.

2. The bracket structure of claim 1, wherein said void space is shaped to produce a deformation in a run of an arch wire received therein, thereby to effect the transmission of a force between such wire run and said first bracket member.

3. For tooth-repositioning use in combination with a run of an arch wire or the like having end portions supported in such a manner that the run tends to seek a predetermined position, the combination in operative condition comprising a first force-transmitter in the form of an insert operatively coupled to said run with a selected orientation which produces a chosen deflection of the run from its said predetermined position, and a second force-transmitter in the form of a twin edgewise bracket force-coupled to a tooth adjacent said run, receiving said first force-transmitter as an insert and holding the same in an omnidirectionally captured condition in its said selected orientation, said first and second force-transmitters having different elastic stiffnesses, with that of said second force-transmitter being greater than that of said first force-transmitter.

4. In combination with an orthodontic arch wire, and the like, and a twin edgewise bracket which includes laterally spaced post structures having forwardly facing, aligned slots intersecting and joining with a pair of substantially parallel-planar confronting faces, an orthodontic device constructed for frontal insertion in said bracket for receiving said wire, said device in operative condition comprising an elongated base portion removably fitted between and seated against said faces whereby the base portion is captured laterally by said post structures, a pair of end projection portions, integral with, and located adjacent, the opposite ends of said base portion, removably fitted in a fore-and-aft captured condition in said slots in said bracket, and means defining a pair of forwardly facing channels formed, one each, in said end projection portions, receiving and deforming a run of said arch wire, thereby effecting the transmission, to said bracket of a tooth-repositioning force.

* * * * *

UNITED STATES PATENT AND TRADEMARK OFFICE
CERTIFICATE OF CORRECTION

PATENT NO. : 4,249,897
DATED : February 10, 1981
INVENTOR(S) : ROLAND M. ANDERSON It is certified that error appears in the above–identified patent and that said Letters Patent are hereby corrected as shown below:

column 8, line 54, delete "omnidirectional" and insert therefor --omnidirectionally--.

Signed and Sealed this

Fifteenth Day of December 1981

[SEAL]

Attest:

GERALD J. MOSSINGHOFF

*Attesting Officer*     *Commissioner of Patents and Trademarks*